United States Patent [19]
Carey et al.

[11] Patent Number: 5,788,928
[45] Date of Patent: Aug. 4, 1998

[54] REAGENT HANDLING SYSTEM AND REAGENT PACK FOR USE THEREIN

[75] Inventors: Glen A. Carey, Grafton; David P. Weber, Strongsville, both of Ohio

[73] Assignee: Chiron Diagnostics Corporation, E. Walpole, Mass.

[21] Appl. No.: 742,014

[22] Filed: Oct. 31, 1996

Related U.S. Application Data

[62] Division of Ser. No. 499,271, Jul. 7, 1995, Pat. No. 5,609,822.

[51] Int. Cl.$^6$ .................. B01F 11/00; G01N 37/00
[52] U.S. Cl. .................. 422/102; 422/63; 422/104; 436/43; 436/180; 366/211; 366/336; 206/219; 220/669
[58] Field of Search .................. 422/63, 65, 100, 422/102, 103, 104; 436/43, 45, 49, 54, 174, 180, 807, 809; 366/210, 211, 216, 208, 209, 81.5, 235–239, 228, 336, 338; 220/669; 206/219

[56] References Cited

U.S. PATENT DOCUMENTS

| | | | |
|---|---|---|---|
| 2,836,979 | 6/1958 | Ryley | 422/100 |
| 3,521,785 | 7/1970 | Bergmann et al. | 220/23.4 |
| 3,578,291 | 5/1971 | Oberli | 366/211 |
| 3,582,283 | 6/1971 | Mirasol Jr. | 23/253 |
| 3,582,285 | 6/1971 | Hamilton | 23/259 |
| 3,643,926 | 2/1972 | Grieve | 366/237 |
| 3,647,397 | 3/1972 | Coleman | 23/309 |
| 3,706,443 | 12/1972 | Oberhauser | 366/211 |
| 3,718,439 | 2/1973 | Rosse et al. | 23/259 |
| 3,804,297 | 4/1974 | Jurjans | 222/54 |
| 3,951,608 | 4/1976 | Trod | 422/102 |
| 3,994,594 | 11/1976 | Sandrock et al. | 356/246 |
| 4,009,999 | 3/1977 | Negersmith | 23/230 R |
| 4,015,938 | 4/1977 | Jay | 23/230 R |
| 4,083,638 | 4/1978 | Sandrock et al. | 356/246 |
| 4,253,846 | 3/1981 | Smythe et al. | 23/230 R |
| 4,259,291 | 3/1981 | Smythe | 422/82 |
| 4,431,606 | 2/1984 | Revillet et al. | 422/102 |
| 4,436,822 | 3/1984 | Eseifan | 436/164 |
| 4,438,068 | 3/1984 | Forrest | 422/61 |
| 4,477,578 | 10/1984 | Miles et al. | 436/518 |

(List continued on next page.)

FOREIGN PATENT DOCUMENTS

| | | |
|---|---|---|
| 2032696 | 6/1991 | Canada . |
| 0109277 | 5/1984 | European Pat. Off. . |
| 0252632 | 1/1988 | European Pat. Off. . |
| 0431352A3 | 11/1990 | European Pat. Off. . |
| 0431352 | 6/1991 | European Pat. Off. . |
| 0632271 | 1/1995 | European Pat. Off. . |
| 58-20227 | 2/1983 | Japan . |
| 1070152 | 3/1989 | Japan . |
| 9205448 | 4/1992 | WIPO . |
| 9320444 | 10/1993 | WIPO . |
| 9320450 | 10/1993 | WIPO . |

*Primary Examiner*—Long V. Le
*Attorney, Agent, or Firm*—Arthur S. Morgenstern; Charles L. Gagnebin, III; Robert P. Blackburn

[57] ABSTRACT

A reagent pack for keeping fluids with or without suspensions mixed or suspended upon rocking. The reagent pack has at least one chamber divided into separate sub-chambers with a throat region between them defined by baffles for agitation of suspended reagent during rocking of the reagent pack. A continuous lid sealable to the pack has membrane sealed apertures in the lid for allowing access to the underlying chambers and sub-chambers by withdrawal needles. A tray is configured to hold multiple side-by-side reagent packs on respective slides that slide in and out for insertion and withdrawal of the packs. During operation, the tray and associated packs are rocked such as by being periodically inclined with respect to horizontal, providing reagent agitation. Optical annunciators proximate the tray indicate respective reagent pack activity under control of a computer which stores information on the contents of each pack at each tray location and correlates it to scheduled reagent use in a medical testing system. The tray is provided with a thermally conductive hinge. The tray with packs is located in an enclosure.

41 Claims, 13 Drawing Sheets

U.S. PATENT DOCUMENTS

| | | | |
|---|---|---|---|
| 4,518,264 | 5/1985 | Nohso | 366/208 |
| 4,551,306 | 11/1985 | Bouwman et al. | 422/56 |
| 4,588,554 | 5/1986 | Kaartinen et al. | 422/61 |
| 4,608,231 | 8/1986 | Witty et al. | 422/61 |
| 4,629,703 | 12/1986 | Uffenheimer | 436/45 |
| 4,663,127 | 5/1987 | Jackson et al. | 422/58 |
| 4,675,299 | 6/1987 | Witty et al. | 436/165 |
| 4,681,741 | 7/1987 | Hanaway | 422/100 |
| 4,708,940 | 11/1987 | Yoshida et al. | 436/45 |
| 4,710,355 | 12/1987 | Ushikubo | 422/100 |
| 4,731,225 | 3/1988 | Wakatake | 422/65 |
| 4,751,184 | 6/1988 | Higo et al. | 435/287 |
| 4,754,414 | 6/1988 | Gocho | 364/497 |
| 4,764,342 | 8/1988 | Kelln et al. | 422/72 |
| 4,774,057 | 9/1988 | Uffenheimer et al. | 422/100 |
| 4,806,311 | 2/1989 | Greenquist | 422/56 |
| 4,812,413 | 3/1989 | Glattstein et al. | 436/92 |
| 4,818,493 | 4/1989 | Coville et al. | 422/102 |
| 4,818,706 | 4/1989 | Starr | 436/180 |
| 4,844,868 | 7/1989 | Rokugawa | 422/64 |
| 4,849,177 | 7/1989 | Jordan | 422/64 |
| 4,861,553 | 8/1989 | Mawhirt et al. | 422/65 |
| 4,865,993 | 9/1989 | Cassady | 436/52 |
| 4,892,833 | 1/1990 | Weiss et al. | 436/97 |
| 4,902,629 | 2/1990 | Meserol et al. | 436/165 |
| 4,925,629 | 5/1990 | Schramm | 422/82.05 |
| 4,927,765 | 5/1990 | Saxon et al. | 436/43 |
| 4,933,147 | 6/1990 | Hollar et al. | 422/64 |
| 4,939,098 | 7/1990 | Suzuki et al. | 436/514 |
| 4,943,164 | 7/1990 | Ohishi et al. | 366/149 |
| 4,944,922 | 7/1990 | Hayashi | 422/100 |
| 4,944,924 | 7/1990 | Mawhirt et al. | 422/104 |
| 4,956,148 | 9/1990 | Grandone | 422/64 |
| 4,970,053 | 11/1990 | Fechtner | 422/102 |
| 4,970,468 | 11/1990 | Ishizawa et al. | 324/662 |
| 4,971,913 | 11/1990 | Manabe et al. | 436/55 |
| 4,985,207 | 1/1991 | Hayashi | 422/102 |
| 4,994,240 | 2/1991 | Hayashi | 422/63 |
| 4,997,768 | 3/1991 | Uffenheimer et al. | 436/45 |
| 5,000,923 | 3/1991 | Coville et al. | 422/102 |
| 5,028,398 | 7/1991 | Hallberg et al. | 422/189 |
| 5,031,797 | 7/1991 | Boris et al. | 222/23 |
| 5,035,861 | 7/1991 | Grandone | 422/64 |
| 5,037,612 | 8/1991 | Takahashi et al. | 422/64 |
| 5,041,267 | 8/1991 | Randtke et al. | 422/102 |
| 5,051,238 | 9/1991 | Umetsu et al. | 422/64 |
| 5,061,450 | 10/1991 | Aoyagi | 422/101 |
| 5,071,034 | 12/1991 | Corbiere | 222/80 |
| 5,091,300 | 2/1992 | Hurni et al. | 435/5 |
| 5,149,501 | 9/1992 | Babson et al. | 422/58 |
| 5,167,922 | 12/1992 | Long | 422/58 |
| 5,183,638 | 2/1993 | Wakatake | 422/64 |
| 5,215,714 | 6/1993 | Okada et al. | 422/64 |
| 5,320,809 | 6/1994 | Dunn et al. | 422/64 |
| 5,324,481 | 6/1994 | Dunn et al. | 422/64 |
| 5,327,948 | 7/1994 | Blakemore | 141/86 |
| 5,501,982 | 3/1996 | Saldivar Jr. et al. | 436/150 |

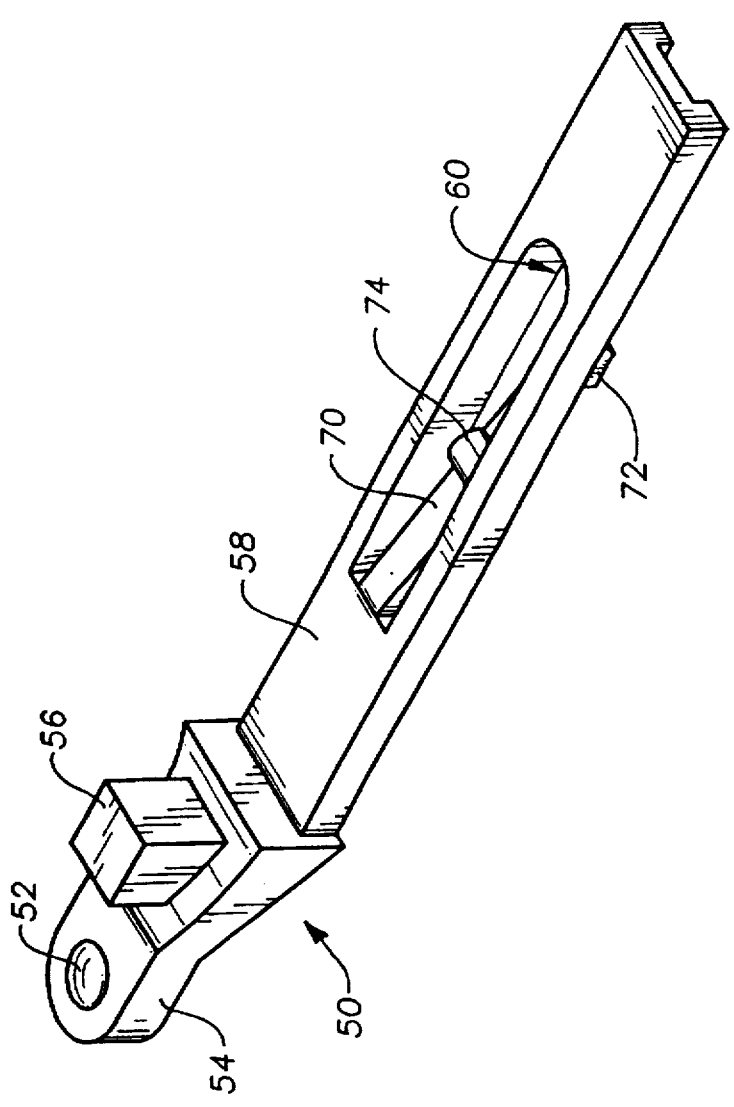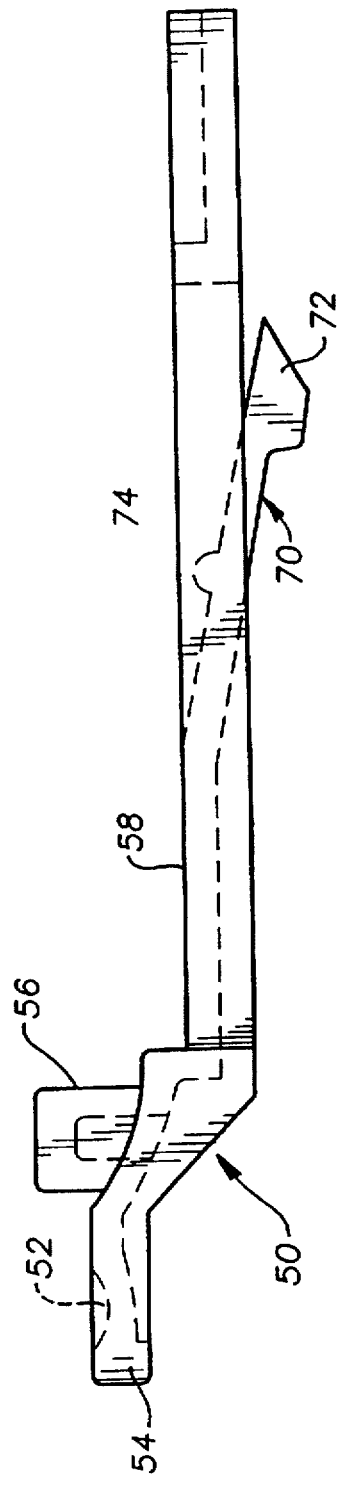

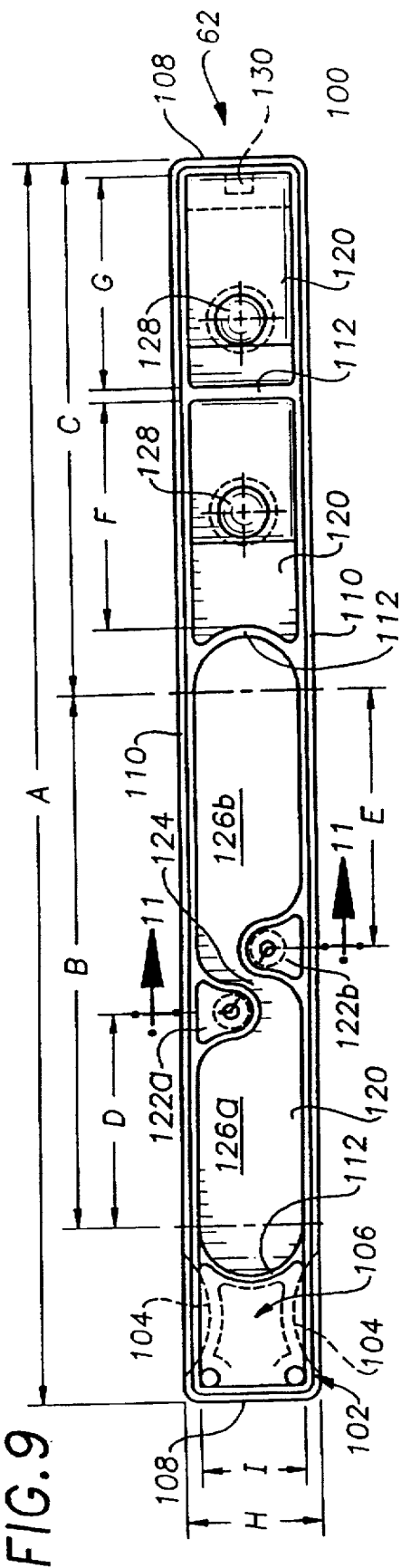

5,788,928

REAGENT HANDLING SYSTEM AND REAGENT PACK FOR USE THEREIN

This is a divisional of application Ser. No. 08/499,271 filed on Jul. 7, 1995, now U.S. Pat. No. 5,609,822.

FIELD OF THE INVENTION

The present invention relates to reagent handling systems and reagent packs for use therein, and in particular to a reagent handling system which inclines reagent packs for reagent agitation.

BACKGROUND OF THE INVENTION

Automated assay devices such as immunoassay instruments provide multiple reagent containers for executing a plurality of individual assays. Storage space for each reagent container has become a significant aspect of instrument design in that more than one reagent is typically required for each assay. Further, the desire to automate dictates that such instruments operate with minimal operator intervention, thus emphasizing the need for adequate quantities of reagent in each container.

Any solid phase reagent, and in particular one including paramagnetic particles, requires physical agitation for uniform suspension in a liquid medium. Further, other materials such as incompatible liquids (e.g. oil and water) require similar agitation for homogenous distribution. Existing means for accomplishing this agitation include axial rotation of cylindrical containers having mixing fins therein. However, such mechanisms are necessarily complex to implement, difficult to maintain, and each require significant physical space. Further, such containers are not accessible during instrument operation. Seals for such containers are typically provided as a "star cap", or resilient cap having star-shaped slits. Such caps provide an insufficient barrier to long-term evaporation and to spillage when the container is tipped.

In general, the most significant requirements for individual reagent containers and for housings holding such containers include the following. Each container should include multiple compartments such that all reagents required for a single assay are accommodated. A sufficient quantity of reagent(s) should be accommodated within each reagent container for unattended execution of a series of tests, such as 50 to 250 assays, or more. The containers should be arranged within the housing for simple removal and installation, even during instrument operation. Evaporation and spillage of reagents stored within the pack should be avoided by provision of improved sealing means. Finally, efficient and mechanically simple solid particle suspension should be implemented, allowing continued mixing during instrument operation.

SUMMARY OF THE INVENTION

The presently disclosed invention provides all the required reagents for multiple iterations of a single assay within minimal space, yet enables mechanically simple and complete admixture of solid reagents within a carrier. Each reagent pack is fully accessible during instrument operation, provided only that reagents from the desired pack are not currently being aspirated or are about to be so aspirated. A pierceable seal in each of multiple reagent pack lid apertures prevents reagent spillage during pack mishandling, minimizes reagent evaporation, and prolongs reagent efficacy. Pack refrigeration further prolongs reagent efficacy.

The present invention provides a reagent pack having at least one chamber for containing all reagents required for a single assay. In a first embodiment, at least one chamber has offset baffles extending from chamber side walls toward the opposing side wall, providing converging and diverging ductwork. The ductwork forms a narrow throat interconnecting two sub-chambers. Suspended reagent or other reactive material flows through this throat region at an accelerated velocity during reagent pack inclination, resulting in agitation and homogenous reagent suspension within each sub-chamber. A continuous lid, sealable to an upper edge of the pack, provides access to underlying chambers via respective apertures in the lid. The reagent pack is disposed on a reagent enclosure tray, and is urged into and out of the enclosure by a respective slide. Provision is made for disposition of multiple packs in a side by side relationship within the enclosure. Inclination of the packs for proper reagent mixing is provided by a motor which periodically tilts the tray back and forth about a central axis.

The reagent packs are accessible to users once a handling system door is lowered. In this position, a number of optical annunciators each corresponding to a respective reagent pack and slide indicate whether the reagent pack is available for manual removal and perhaps replacement. Tray inclination is inhibited during such access. Efficacy of reagents within the enclosure is prolonged by cooling means such as thermal electric devices and heat sinks disposed proximate the enclosure.

BRIEF DESCRIPTION OF THE DRAWINGS

These and other features of the present invention are more fully set forth below in the fully exemplary detailed description and accompanying drawings of which:

FIG. 3 is a perspective view of a reagent pack slide as used in the reagent handling system of FIG. 2;

FIG. 4 is a side view of the slide of FIG. 3 showing internal details in phantom;

FIG. 9 is a top view of a reagent pack as used in the reagent handling system of FIG. 2;

FIG. 10 is a side sectional view of the reagent pack of FIG. 9;

DETAILED DESCRIPTION

Figure 1:
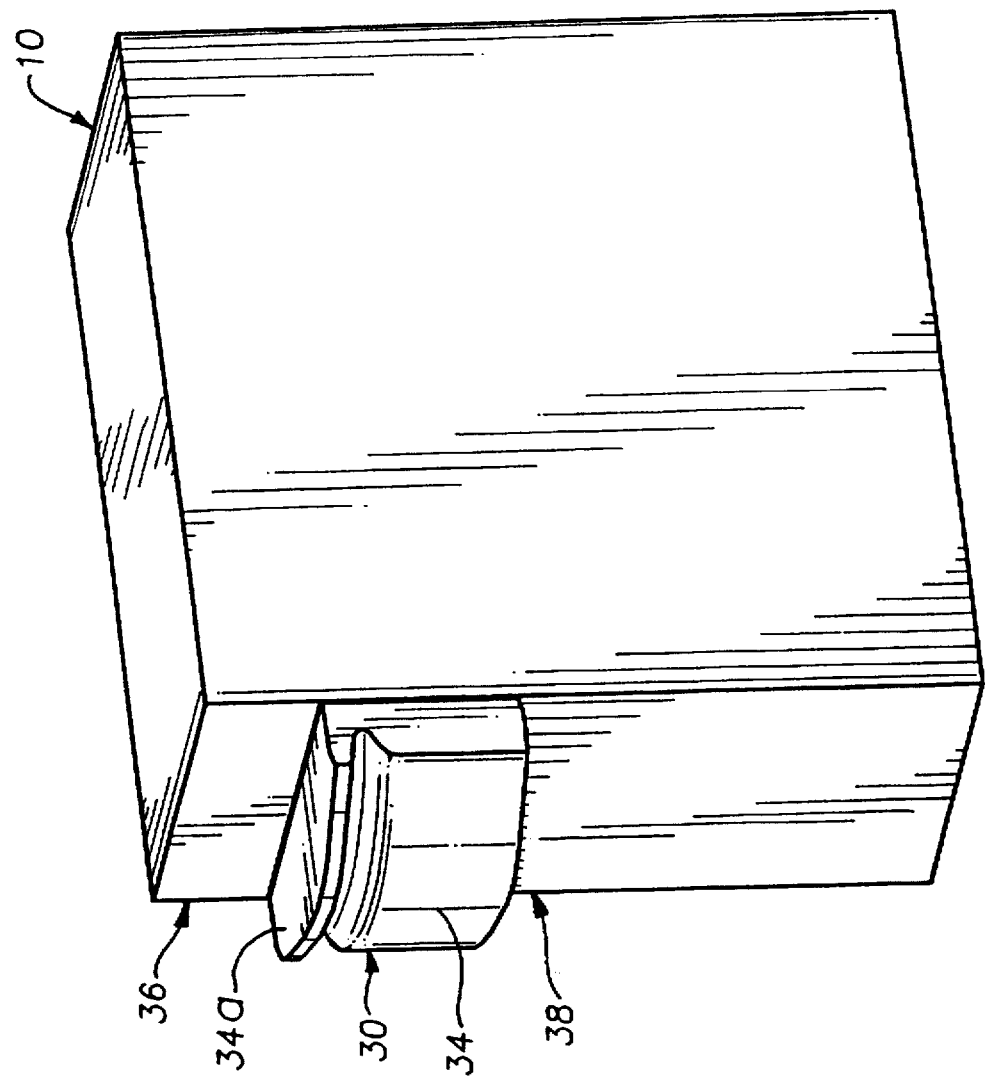
FIG. 1 is a perspective view of an automated analyzer system of which the presently described and claimed reagent handling system forms a part.

Referring now to FIG. 1, an automated analyzer system 10 for performing assays includes a reagent handling system 30 which here is covered by a reagent door 34 having a shelf portion 34a. Located above the reagent handling system 30 is a probe system 36 which aspirates reagents from the reagent system 30 and dispenses the reagents at predetermined locations of the analyzer instrument 10. The analyzer system further includes a refrigeration unit 38 which is provided to cool reagents installed in the analyzer system 10, and in the reagent handling system 30 in particular. The reagent handling system 30 and refrigeration unit 38 will each be described in further detail subsequently.

Figure 2:
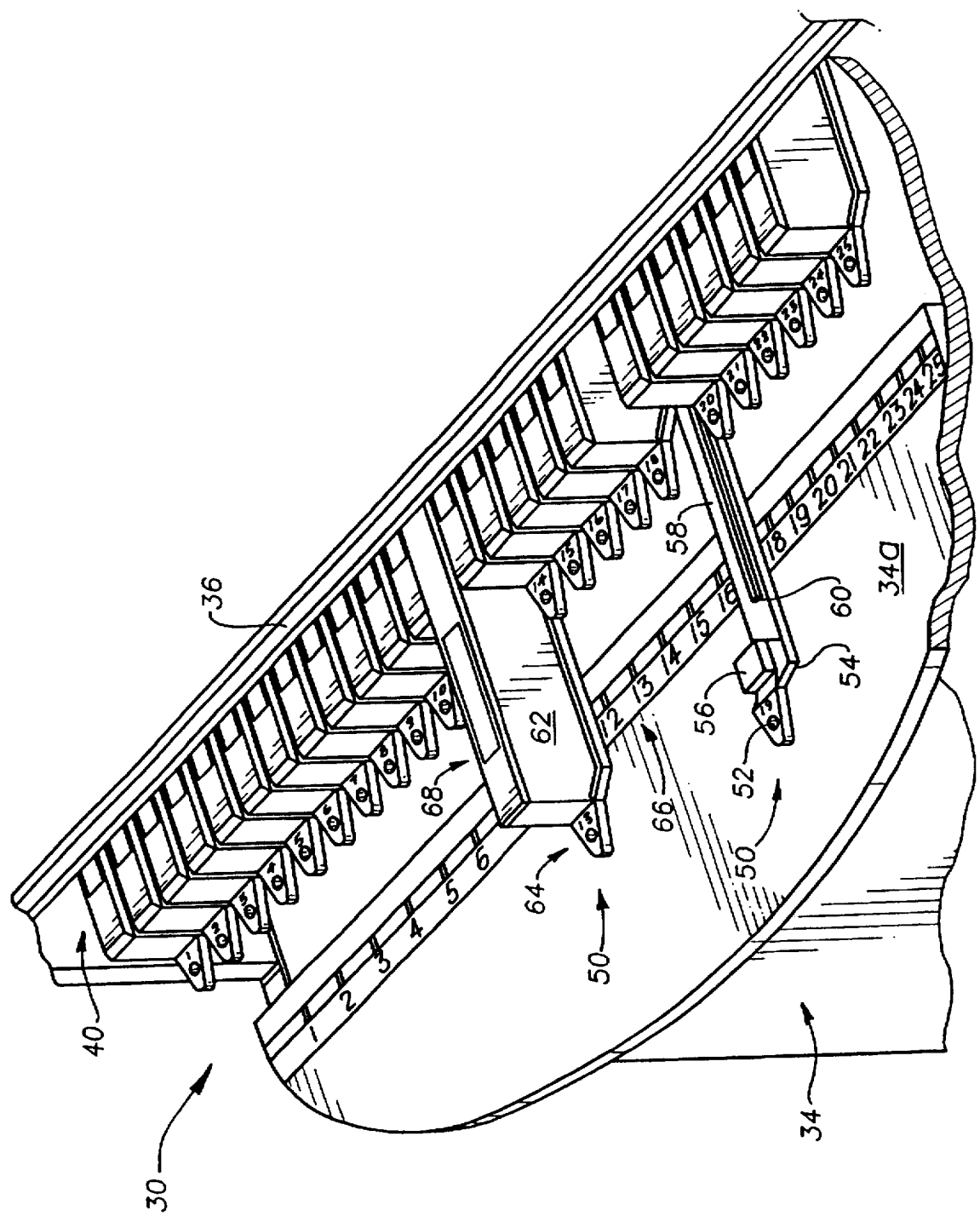
FIG. 2 is a partial perspective view of the reagent handling system as used in the automated analyzer system of FIG. 1.
Figure 5:
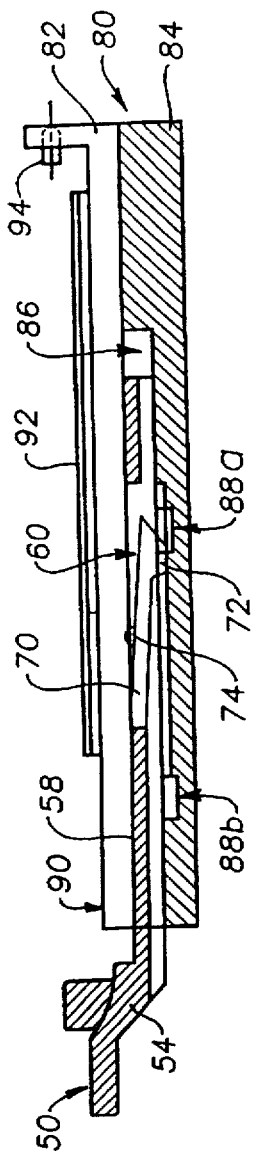
FIGS. 5 through 8 are side views of the slide of FIG. 4 installed to varying degrees within a tray of the reagent handling system of FIG. 2.

With regard to FIG. 2, a portion of the reagent handling system 30 is now described. A reagent door 34, which is shown in an elevated, or closed, position in FIG. 1 is shown in a lowered, or open, position in FIG. 2. Rails (not illustrated) or similar means are employed for maintaining the door 34 in proper alignment with the system 30 in either position. Once the door 34 is lowered, multiple reagent packs 62 are seen disposed in a side-by-side relationship proximate respective reagent pack slides 50 within an enclosure generally designated as 40. As will be described further below, the reagent enclosure provides a refrigerated atmosphere which extends the useful life of the reagents or other reactive materials disposed in reagent packs 62 therein. A refrigeration unit 38 (FIG. 1) provides the low temperature atmosphere within the reagent enclosure 40.

Each slide 50, as the name implies, is translatable from an installed position within the reagent handling system 30 and enclosure 40 to a load position in which a portion of the extended slide 50 protrudes over the reagent door shelf 34a. In an illustrative embodiment of the present invention, thirty slides 50 accommodate a like or smaller number of reagent packs 62, each slide being formed of a polycarbonate resin such as Lexan (General Electric Company). The majority of the slides 50 in FIG. 2 are illustrated in the installed position.

With regard also to FIGS. 3 and 4, each slide 50 provides a handle 54 and thumb depression 52 for manually transitioning the slide 50 between the installed and load positions. A reagent pack 62 having a cavity on a bottom surface (discussed subsequently) is disposed proximate a slide upper carrying surface 58 having a post 56, the latter extending into a bottom surface cavity of the reagent pack 62 for maintaining the position of the pack 62 relative to the slide. Each reagent pack 62 is thus safely retained above the respective slide 50 during installation and withdrawal, and during reagent pack inclination, as described below.

In a preferred embodiment, each slide 50 is further provided with a label 64 (FIG. 2) on the slide handle 54 for identifying the relative position of the slide 50 within the row of slides. The slide label 64 corresponds to a numbered optical annunciator 66 such as an LED disposed on the shelf portion 34a of the reagent door 34. When the door 34 is lowered to expose the slides 50 and associated reagent packs 62, illuminated LEDs 66 indicate that the corresponding reagent pack 62 is being accessed by the probe system 36, as described in further detail below, and is therefore prevented from being withdrawn. Once the associated LED 66 is extinguished, this indicates that the reagent pack 62 is not now being accessed or is not about to be accessed by the probe system 36, and is available for withdrawal by pulling the slide 50 outward.

The slides 50 are maintained in side-by-side relationship on a tray, generally designated as 80 in FIGS. 5 through 8. In one embodiment, the tray 80 is provided in at least two parts, a tray upper half 82 and a tray lower half 84. The lower half 84 provides a slot 86 into which the slide extends. In order to maintain the slide 50 in the installed or load positions, or in between, a resilient arm 70 is disposed in a longitudinal slot 60 on the slide 50. This arm 70 has a neutral position which is angled down, for instance, approximately eight degrees from the upper carrying surface 58 of the slide 50.

Figure 6:
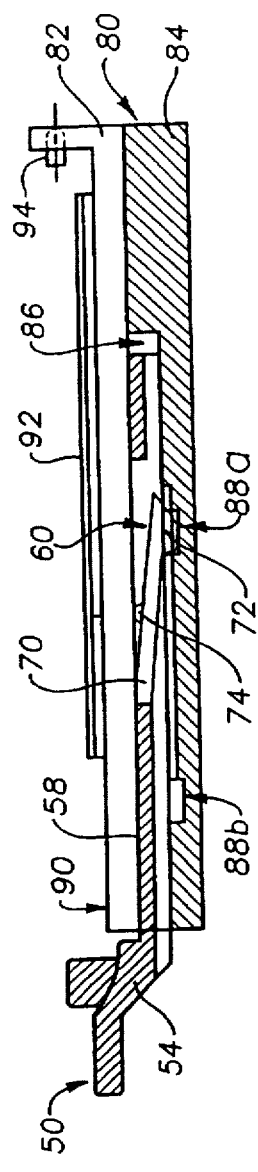

The bottom surface of the slot 86 has two recesses 88a, 88b. When the slide 50 is fully inserted into the tray 80, an end portion 72 of the slide resilient arm 70 is urged into the forward recess 88a, as illustrated in FIG. 6. The forward recess 88a is relatively shallow, thus allowing the end portion to be removed from the recess 88a as in FIG. 5 by a moderate rearward force, such as exerted by a user pulling the slide 50 out, or to the left as shown.

Figure 7:
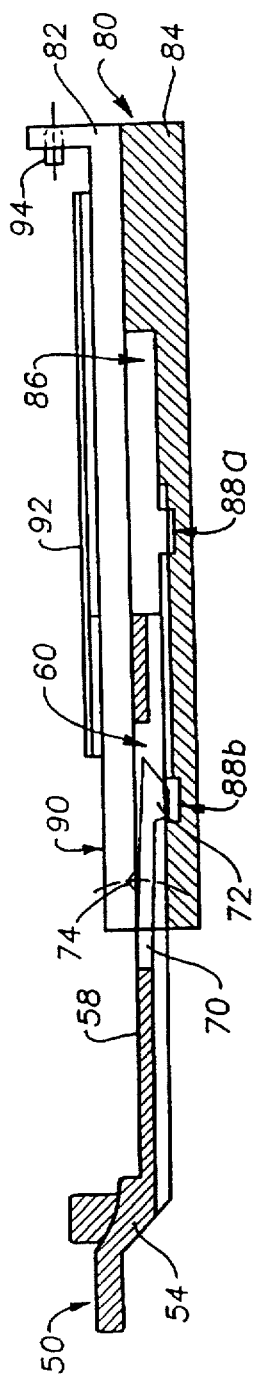

When a user pulls the slide swiftly to the left, the end portion 72 of the arm 70 is brought into contact with a portion of the lower tray 84 which prevents the removal of the slide 50 entirely without the use of a tool such as a narrow screw driver or fingertip to further elevate the arm 70 and end portion 72. In FIG. 7, the arm 70 has been pushed upward by such a tool so that the end portion 72 is level with an upper surface of the tray lower half 84.

In order to prevent inadvertent withdrawal of the slide 50, the arm 70 is further provided in the illustrated embodiment with a knob 74 which contacts a lower surface of the tray upper half 82 before the arm end portion 72 is elevated enough for slide withdrawal. The effect of the knob 74 pressing against the tray upper half 82 is to shorten the length of the flexible arm 70, thus providing a stiffer arm 70 which offers more resistance to upward motion. In the illustrated embodiment, the knob 74 cuts the arm 70 length roughly in half, thus effectively doubling the arm 70 spring constant.

Figure 8:
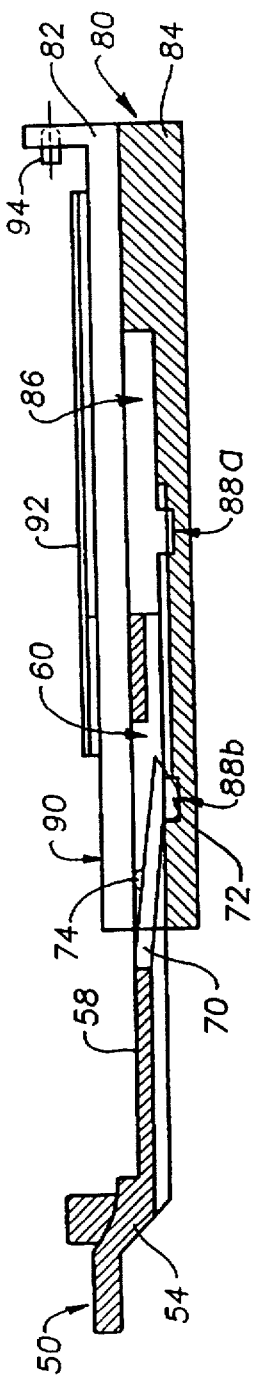
Figure 11:
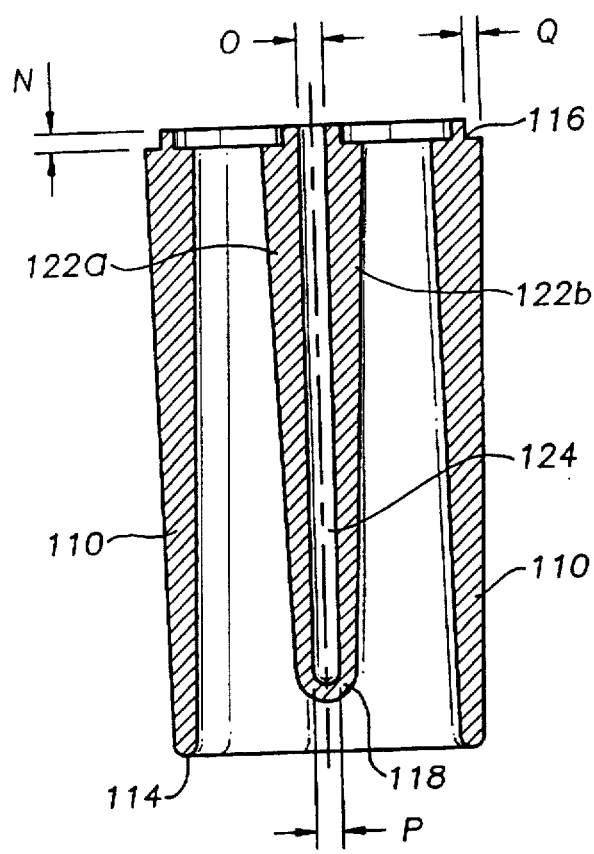
FIG. 11 is a cross-sectional view of the reagent pack of FIG. 9.

In a normally withdrawn or extended position, the end portion 72 extends into the rearward recess 88b, as in FIG. 8. Subsequent insertion of the slide into the tray 80 is accomplished by pushing the slide handle 54 to the right, thus causing the end portion 72 to become disengaged from the rearward recess 88b. Over-insertion of the slide 50 is prevented by the proximity of the slide handle 54 to the tray upper half 82 when the slide 50 is fully inserted, shown in FIG. 6.

As shown in FIGS. 5 through 8, the slide 50 is inserted under the tray upper half 82. An upper surface 90 of the tray upper half 82 provides a surface for a reagent pack 62 to slide across as the pack 62 is inserted into the reagent handling system 30. Thus, while the reagent pack 62 is installed over the slide post 56, the reagent pack 62 actually rides on the upper surface 90 of the tray upper half 82. The reagent pack 62 itself will be described in further detail below. However, to improve the efficiency of reagent pack 62 cooling via the tray 80 acting as a cold plate, it is noted that elevated portions 92 of the tray upper half 82 minimize an airgap between a bottom surface of the reagent pack 62 and the tray 80, thus improving thermal conductivity. Further, a retaining pin 94 or similar device is disposed on the tray upper half 82 for engagement with a cooperating reagent pack receptacle (described below), thus ensuring proper alignment of the reagent pack within the tray 80.

The reagent packs 62 visible in FIG. 2 proximate respective slides 50 are now described in greater detail with respect to FIGS. 9 through 12. The reagent packs are formed of high density polyethylene (HDPE) in a first embodiment. Other materials are employable taking into consideration the requirement that the material chosen be non-reactive with the intended pack contents. Cost is another important consideration for pack materials in some embodiments.

FIGS. 9 and 10 illustrate a reagent pack 62 having a forward end 100 and a rearward end 102. In FIG. 2, the forward end 100 is inserted within the reagent handling system 30, and the rearward end 102 is visible proximate the slide handle 54. In a preferred embodiment of the present invention, the rearward end 102 has a pinched region 104 which facilitates manual manipulation of the reagent pack 62. Disposed within the pinched region 104 and disposed within a lower surface thereof is a cavity 106 which receives the slide post 56, thus enabling the slide 50 to usher the reagent pack 62 into and out of the handling system 30.

The reagent pack illustrated in FIGS. 9 and 10 is partially defined by end walls 108, side walls 110, and intermediate walls 112. While the end and side walls 108, 110 extend from a lower edge 114 of the reagent pack 62 to an upper edge 116, not all of the intermediate walls 112 extend down to the lower edge 114. Rather, a floor surface 118 is disposed proximate but slightly above the lower edge 114, and the intermediate walls 112 extend from this surface 118. Together, these walls and surfaces divide each reagent pack interior into a plurality of chambers 120. The floor surface 118 within each of these chambers is canted toward one location, in a first embodiment, in order to facilitate complete withdrawal and usage of material stored therein. In a preferred embodiment, this location takes the form of a depression 128 in the floor surface 118 at a rear portion of each chamber.

Each of the aforementioned chambers 120 are intended for storage of reagents used by the analyzer system 10. In certain cases, the reagent is soluble, and thus requires little or no agitation for homogenous distribution within the chamber 120. Other reagents, however, are not soluble, and do require agitation for continuous distribution throughout the respective chamber 120. As a result, at least one of the chambers of each reagent pack according to the present invention is provided with a pair of opposing, offset baffles 122a, 122b.

These baffles 122a, 122b, each of which extend from a respective side wall 110 toward the opposite side wall 110, are vertically disposed from the floor surface 118 to the upper edge 116 of the side wall 110, and preferably extend across at least half the width of the reagent pack 62 toward the opposing side wall 110. Further, while one of the baffles 122a is disposed closer to the reagent pack rearward end 102 than the other baffle 122b, they are close enough to one another to form a ductwork having converging then diverging walls, otherwise referred to as a narrow throat 124 within the respective chamber 120. The baffles are illustrated in the composite sectional view of FIG. 11, and while being omitted from the side sectional view of FIG. 10 for clarity.

Figure 12:
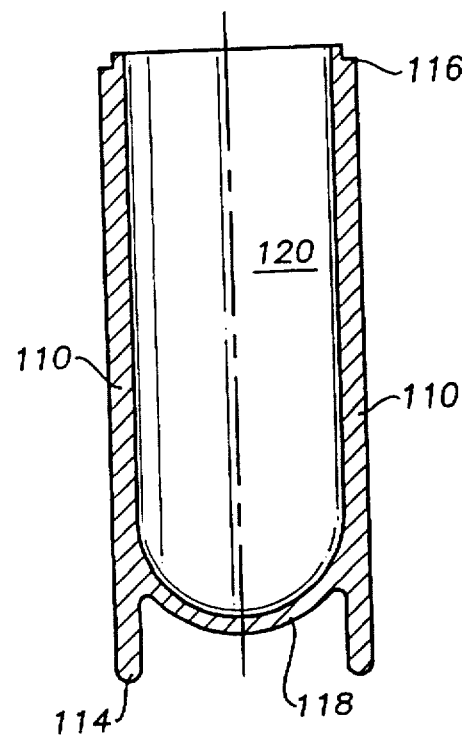
FIG. 12 is a cross-sectional view of the reagent pack of FIG. 9.

In particular, the larger chamber 120 in FIG. 9 and shown in representative cross-section in FIG. 12 is shown divided into two sub-chambers 126a, 126b of substantially equal volumes, each of the sub-chambers 126a, 126b interconnected by the throat 124. The benefit of such a configuration is realized when suspended reagent materials are introduced into this divided chamber 112, and the reagent pack 62 is tilted back and forth about an axis under the reagent pack and orthogonal to the slide 50. Fluent material, carrying the suspended reagent, greatly accelerates as it passes through the throat 124, resulting in significant agitation of the reagent and fluent carrier through currents circulating about the perimeter of the sub-chambers. Complete, homogenous distribution is achieved rapidly, with the exact speed of mixing depending upon the angle of tilt, the frequency of oscillation, the reagent intermixed, the fluent carrier, and the reagent temperature. Means for tilting the tray 80 and the reagent pack 62 disposed thereon are described in detail below.

As previously noted, the reagent pack 62 is installed over a respective slide 50, including a slide post 56, but the reagent pack weight is principally borne by the tray upper half upper surface 90, the lower edge 114 of the pack 62 gliding thereon. The slide is therefore used primarily to impart relocating force to the reagent pack 62 and to retain the reagent pack 62 in the desired position within the handling system 30. Also as previously noted, the tray upper half 82 has a retaining pin 94 (FIGS. 5 through 8) which is received within a reagent pack receptacle 130 (FIGS. 9 and 10) formed proximate the lower edge 114 of the end wall 108 at the forward end 100 of the reagent pack 62. This arrangement ensures the proper alignment of the reagent pack 62 to the remainder of the handling system 30.

Exemplary dimensions for the illustrated reagent pack and for alternative embodiments are provided in table 1. All measurements are provided in inch units.

TABLE 1

| DIMENSION | EMBODIMENT 1 | EMBODIMENT 2 | EMBODIMENT 3 |
|---|---|---|---|
| A | 6.69 | 6.69 | 6.69 |
| B | 3.00 | 2.40 | 3.00 |
| C | 2.83 | 3.13 | 2.83 |
| D | 1.32 | 0.89 | 1.32 |
| E | 1.32 | 0.89 | 1.32 |
| F | 1.15 | 1.15 | 1.15 |
| G | 1.20 | 1.20 | 1.20 |
| H | 0.72 | 1.320 | 0.72 |
| I | 0.60 | 1.20 | 0.60 |
| J | 1.895 | 1.895 | 1.895 |
| K | 0.89 | 0.89 | 0.89 |
| L | 1.665 | 1.665 | 0.83 |
| M | 1.449 | 1.449 | 0.600 |
| N | 0.060 | 0.060 | 0.060 |
| O | 0.082 | 0.113 | 0.082 |
| P | 0.072 | 0.103 | 0.072 |
| Q | 0.030 | 0.030 | 0.030 |

Note that in Embodiment 2, the reagent pack is over twice as wide (dimension H) as that of Embodiment 1, thus requiring two adjacent slides 50 for insertion and removal. This embodiment obviously provides a greater quantity of reagent or other reactive material, and thus enables execution of a greater number of assays before pack 62 replacement.

An illustrative embodiment of a reagent pack according to the present invention is illustrated in FIGS. 19 through 25.

Figure 13:
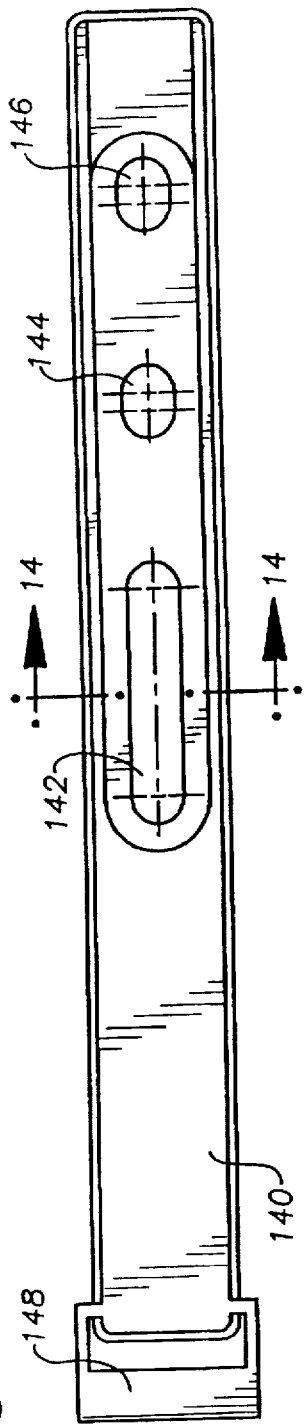
FIG. 13 is a top view of a reagent pack lid as used in the reagent handling system of FIG. 2.
Figure 14:
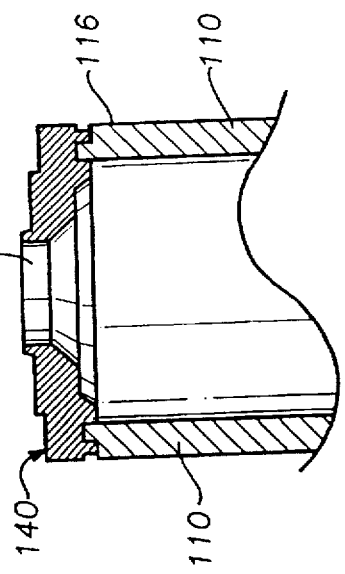
FIG. 14 is a partial cross-sectional view of the lid of FIG. 13 disposed atop the reagent pack of FIG. 9.
Figure 15:
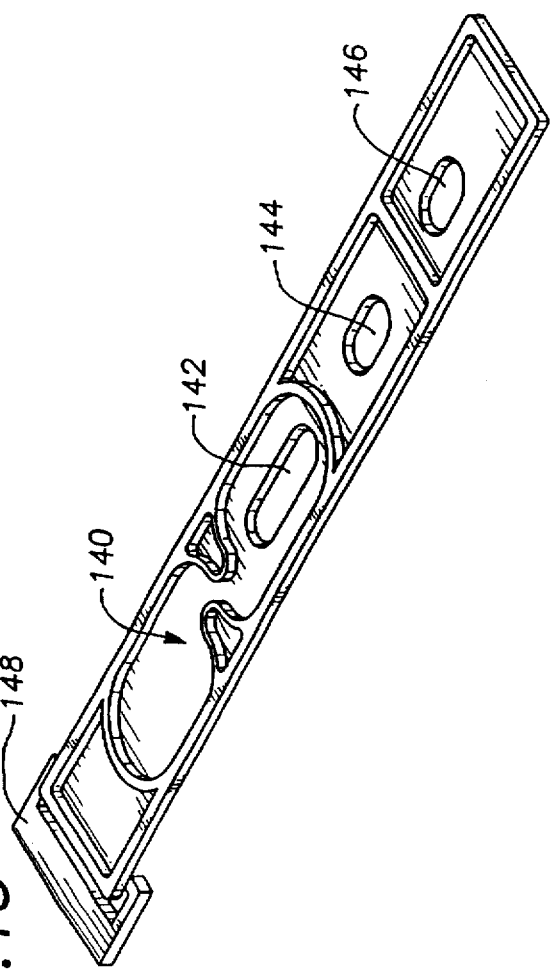
FIG. 15 is a bottom perspective view of the lid of FIG. 13.

In FIGS. 13 through 15, a lid 140 for a reagent pack is illustrated. The lid 140, formed of HDPE in a first embodiment, includes plural apertures 142, 144, 146. Each aperture 142, 144, 146 is covered with a penetrable material such as a combination of polyester and ethyl vinyl acetate (EVA) films in one embodiment, or a combination of polyester and HDPE films in another. Alternatively, a single layer of film is employed. In all embodiments, an important criteria is that the aperture covering material be inactive with the enclosed reagent. The apertures 142, 144, 146 are substantially aligned with respective underlying chambers 120, and preferably with reagent pack chamber floor depressions 128. A needle-like probe, part of the probe system 36, passes through the aperture by penetrating the covering material and extends into a quantity of material such as reagent contained therein for aspiration and use elsewhere in the system 10. The lid 140 is hot plate welded onto the upper edge 116 of the reagent pack 62 aperture in one embodiment. The aperture covering material significantly reduces leakage or spillage which result from improper manipulation of the reagent pack.

In a preferred embodiment, the lid 140 is attached to an empty reagent pack 62 shell as previously described. The reagent pack 62 is filled, after which the aperture covering material is applied. Each aperture may be covered separately, or all my be covered by a continuous portion of aperture covering material at once. The reagent pack lid 140 further comprises, in the embodiment illustrated in FIGS. 13 and is, a tab 148 useful during pack 62 assembly. The tab 148 provides a convenient hand hold when the lid 140 is positioned for attachment to the pack 62. Other embodiments for the tab 140 are possible. After assembly, the tab 148 is removable.

Figure 16:
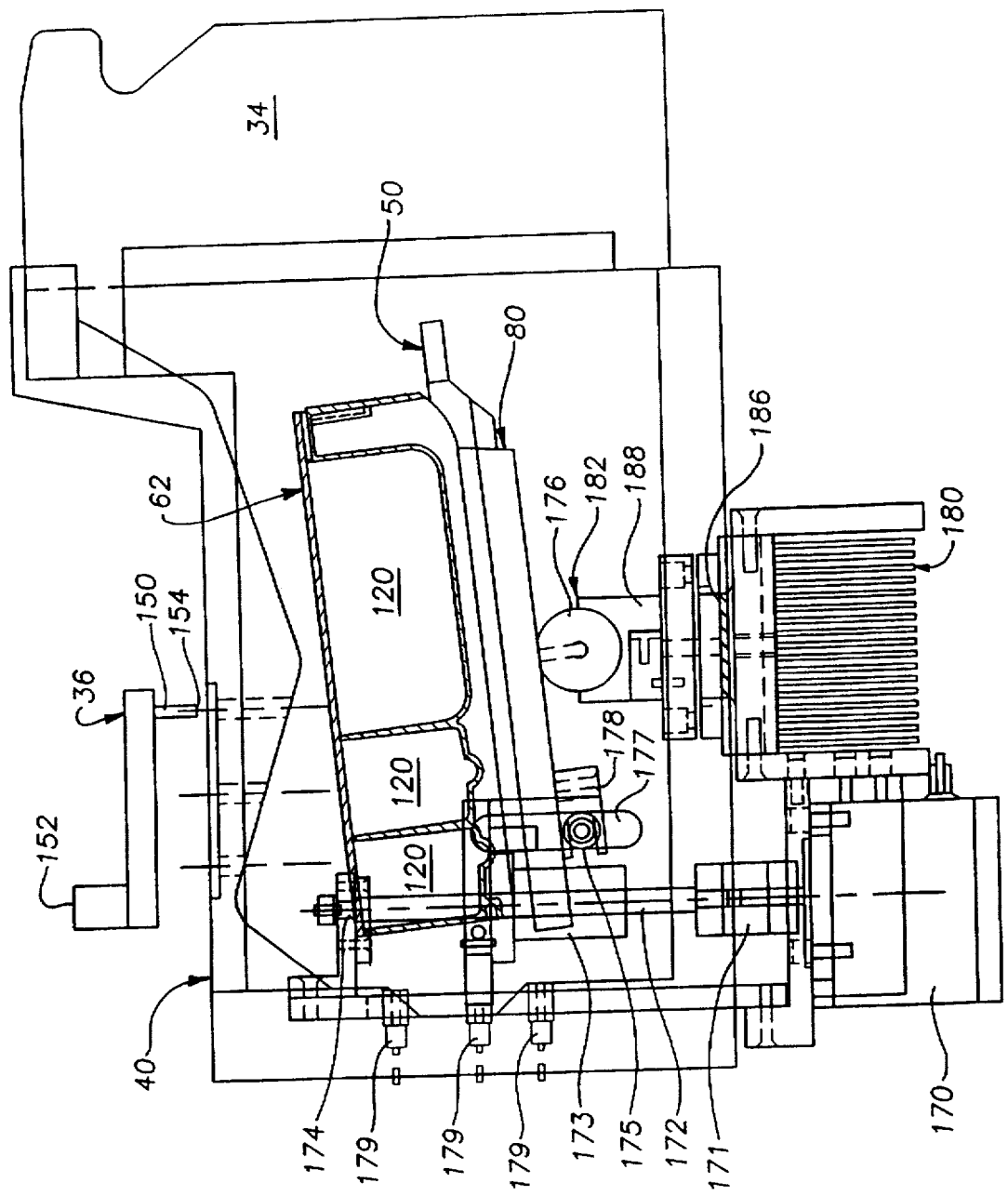
FIG. 16 is an end view of a reagent pack enclosure as used in the reagent handling system of FIG. 2.

The general placement of the probe system 36 with respect to the enclosure 40 is illustrated in FIG. 16, and includes a motor 152 for translating at least one probe tip 154 across and above the reagent packs 62 disposed on the tray 80 in a direction of motion orthogonal to the direction of motion of the slides 50. Further motive means are provided in the probe system 36 for translating the probe tip 154 along the length of a given reagent pack 62. Thus, the probe tip 154 is capable of being positioned above any of the lid apertures 142, 144, 146 and associated chambers 120. A third motive means associated with the probe system 36 controls the vertical position of the probe tip 154. In one embodiment of the present invention, each motive means is provided in the form of one or more stepper motors. In another embodiment of the present invention, three probes 150 are provided within the probe system 36, thus enabling coincidental aspiration between the probes 150.

In another embodiment of the present invention, a bar code label (not illustrated) is disposed on the forward end 100 of the each reagent pack 62 to provide information about the contents of the pack 62 such as type of reagent, quantity, concentration, expiration date, etc. This information is scanned by a bar code reader (not illustrated) disposed within the analyzer system 10 and translated by motive means such as a stepper motor.

In alternative embodiments of the present invention, other means for passing information from a reagent pack to the analyzer system 10 are envisaged. For instance, relevant information may be magnetically encoded in a stripe on the forward end 100 of a reagent pack 62. A magnetic stripe reader would then be employed by the system 10. Further, other optical data transfer techniques are employable, such as optical character recognition.

As previously noted, each reagent pack 62 is disposed above a respective slide 50 and on a portion of a tray 80 within the enclosure 40. In order to preserve the efficacy of reagents or other reactive materials disposed within the reagent packs 62, it is preferred that the enclosure 80 be insulated and refrigerated, with the tray 80 preferably provided in teflon-coated aluminum to act as a cold plate. Thermo-electric devices (TEDs) 186 (four, in one embodiment) are disposed proximate to and in thermal communication with an inclination pin 176 through a thermally conductive bearing surface block 188. Together, the inclination pin 176 and the bearing surface block 188 form a thermally conductive hinge 182. Thus, the reagent packs 62 can be inclined about this hinge, the hinge being capable of conducting heat through the bearing surface block 188 to the TEDs 186. Such cold plate cooling is more efficient than air cooling, the latter suffering from loss of cooling effect when the door 34a is opened.

In an exemplary embodiment, a thermistor (not shown) associated with each TED 186 is installed within the enclosure 40 for providing a TED control circuit with feedback regarding the current thermal state of the enclosure 40. The TEDs 186 are further provided with heat sinks 180 below the enclosure 40 in order to enhance the effectiveness of the TEDs. A fan (not illustrated) is provided proximate the fixed heat sink 180 in a further embodiment to further enhance the efficiency of the TEDs 186.

The tray 80, on which the reagent packs 62 rest and in which the slides 50 are disposed, provides support for the packs 62 within the refrigerated reagent enclosure 40. As previously described, the reagent packs 62 are preferably provided with a unique set of mixing baffles 122 which cause turbulence within at least one of the reagent pack chambers 120 when the pack 62 is tilted along its length. Thus, it is desired that the reagent tray be capable of inclination about an axis orthogonal to the direction of motion of the slides 50 and parallel to the axis along which the multiple reagent packs 62 are disposed within the reagent tray enclosure 40.

Also visible in FIG. 16 is an inclination motor 170 disposed, depending upon the embodiment, at either end or in the middle of the enclosure 40 for providing the power required to incline the tray 80. Preferably, the inclination motor 170 is a stepper motor. Extending axially from the inclination motor 170 is a screw shaft 172 mounted in bearings 174 at the top end of the shaft 172 and coupled to the motor via a coupling 171. Rotation of the shaft 172 causes a follower nut 173 to travel up or down the screw shaft 172, depending upon the direction of rotation. A rocker shaft 175 is affixed to the follower nut 173, is disposed along the length of the enclosure and is mechanically affixed under the tray 80 by a slide block 178. When the follower nut 173 is driven up or down by rotation of the screw shaft 172, the rocker shaft 175 similarly travels up or down in a support bracket channel 177, resulting in the inclination of the tray 80 and associated reagent packs 62 about the pivot shaft 176 which extends parallel to the rocker shaft 175. In a preferred embodiment, the limits of tray 80 inclination are twenty degrees above and below horizontal, though other angular limits are possible depending upon the enclosure space and mixing requirements. Sensors 179 are provided for detecting the angle of inclination.

Figure 17:
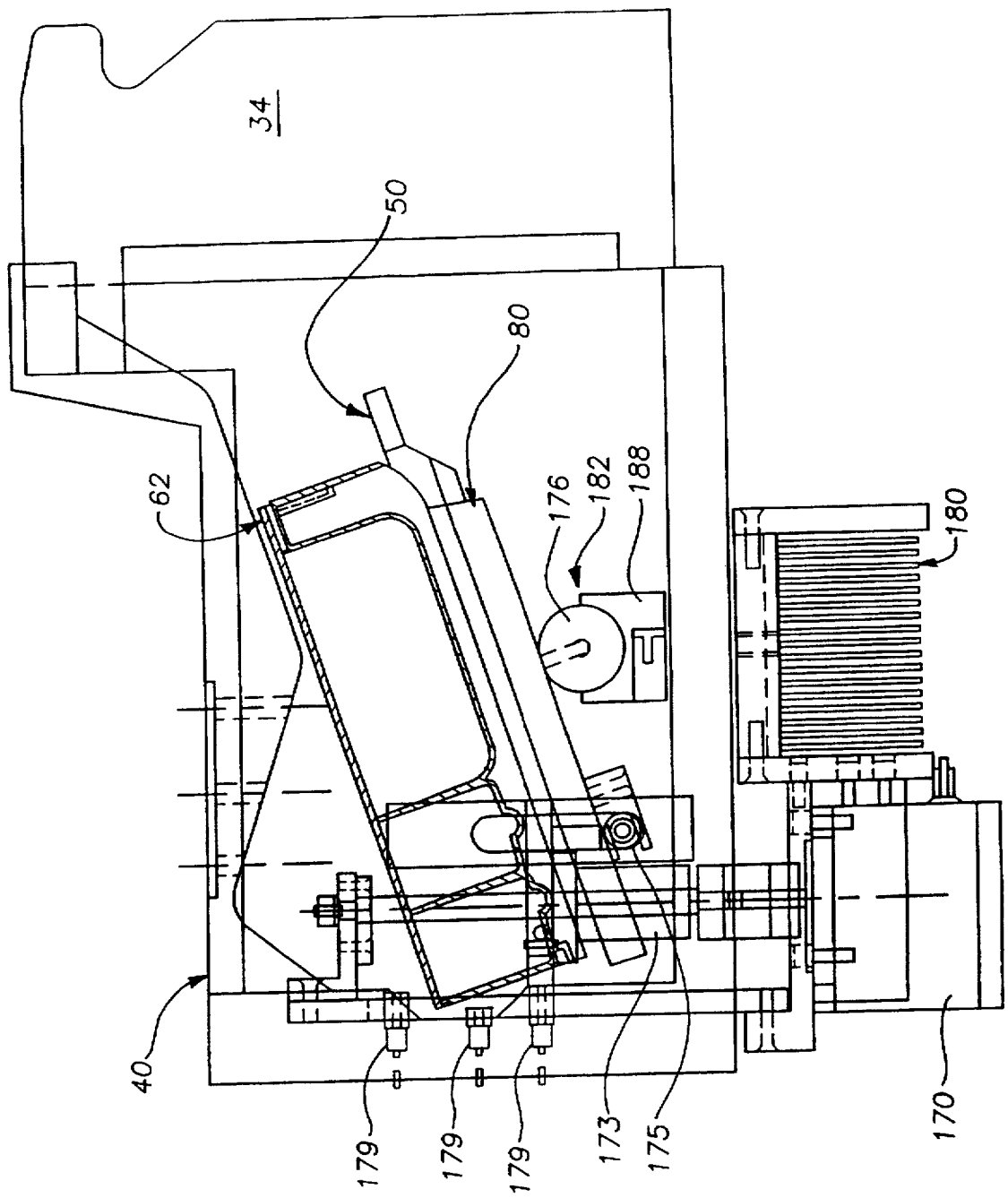
FIG. 17 is a simplified end view of the enclosure of FIG. 16 in a first position.
Figure 18:
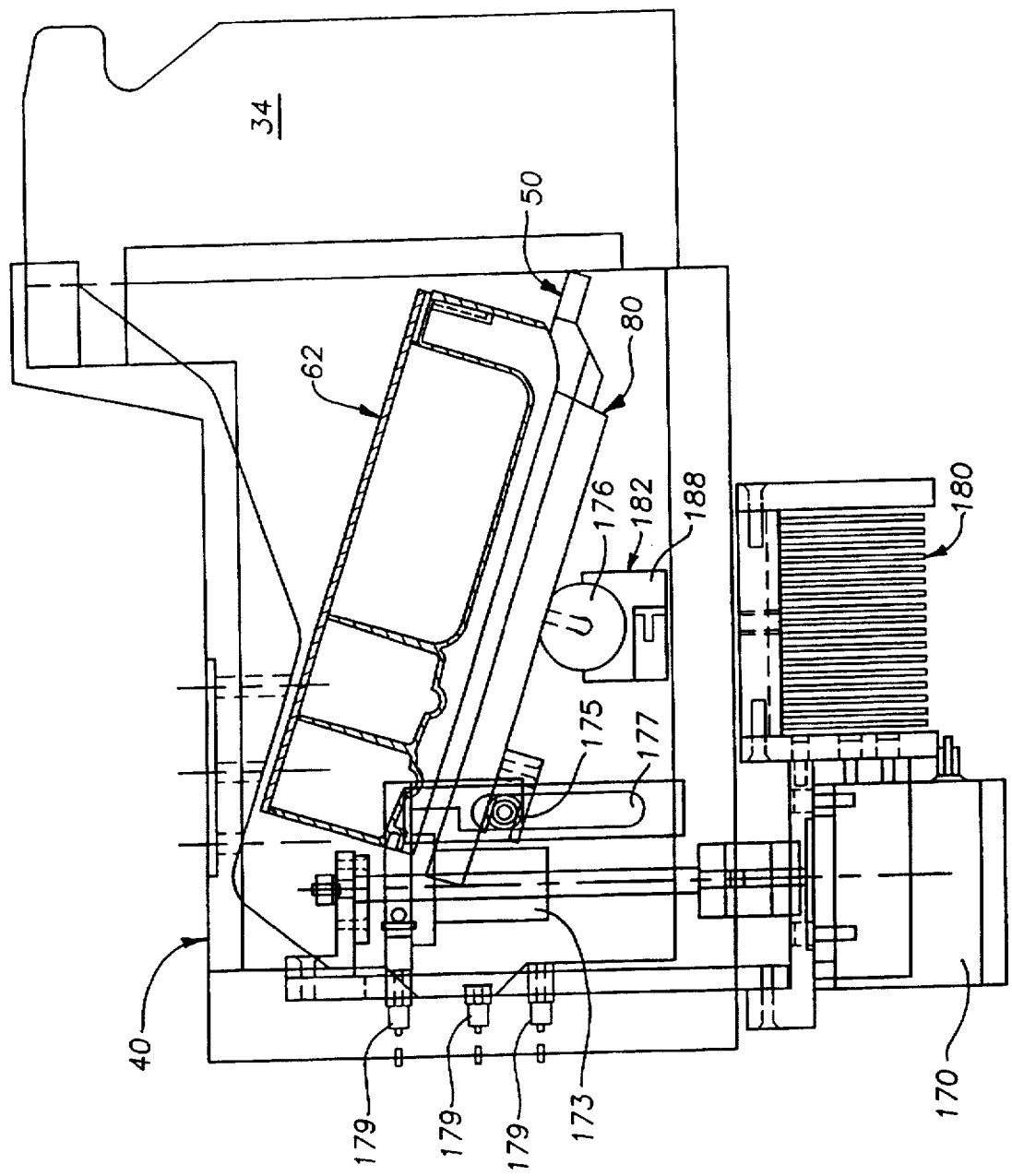
FIG. 18 is a simplified end view of the enclosure of FIG. 16 in a second position.
Figure 19:
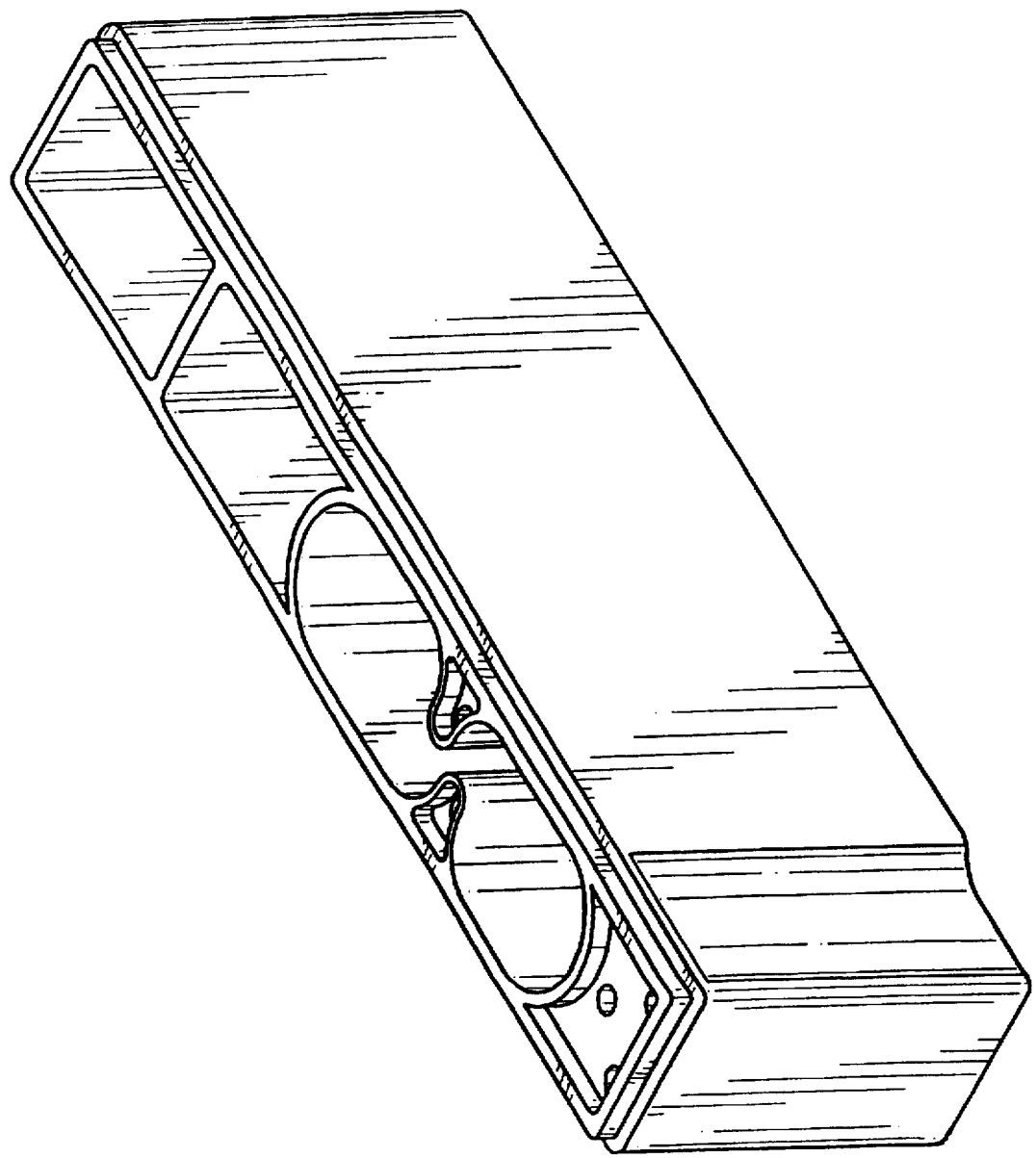
FIG. 19 is a top-right-front perspective view of a reagent pack as used in the reagent handling system of FIG. 2.
Figure 21:
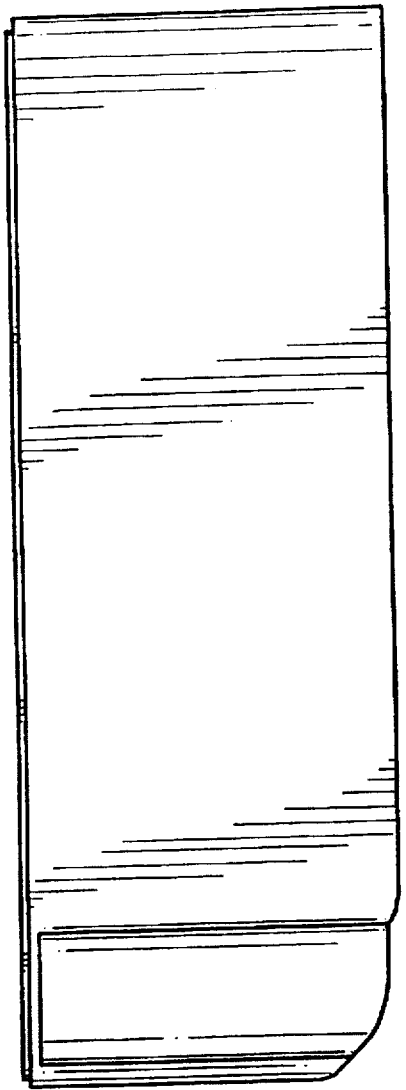
FIG. 21 is a right side view of the reagent pack of FIG. 19.
Figure 20:
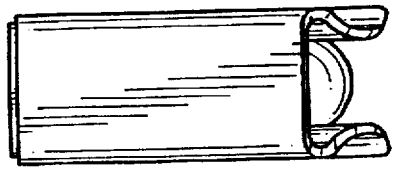
FIG. 20 is a front end view of the reagent pack of FIG. 19.
Figure 23:
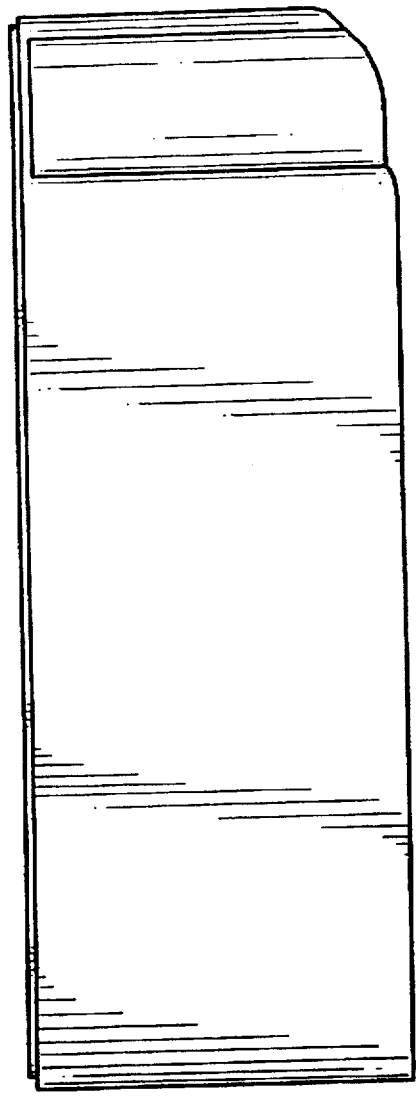
FIG. 23 is a left side view of the reagent pack of FIG. 19.
Figure 22:
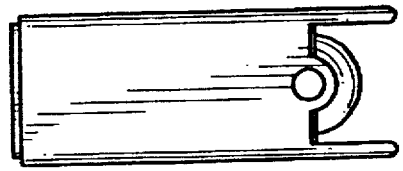
FIG. 22 is a rear end view of the reagent pack of FIG. 19.
Figure 24:
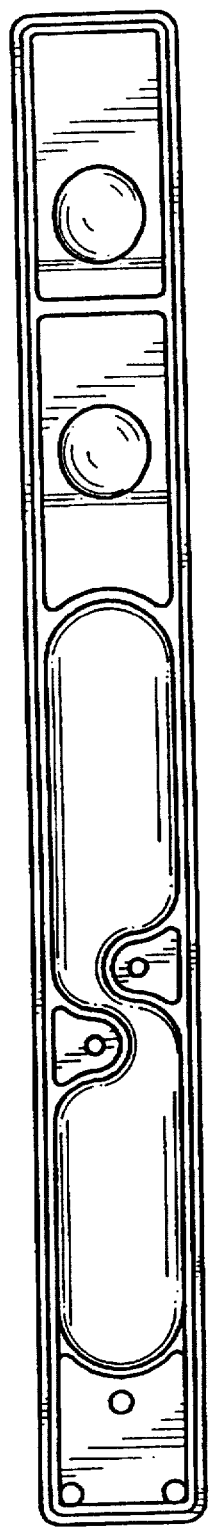
FIG. 24 is a top view of the reagent pack of FIG. 19.
Figure 25:
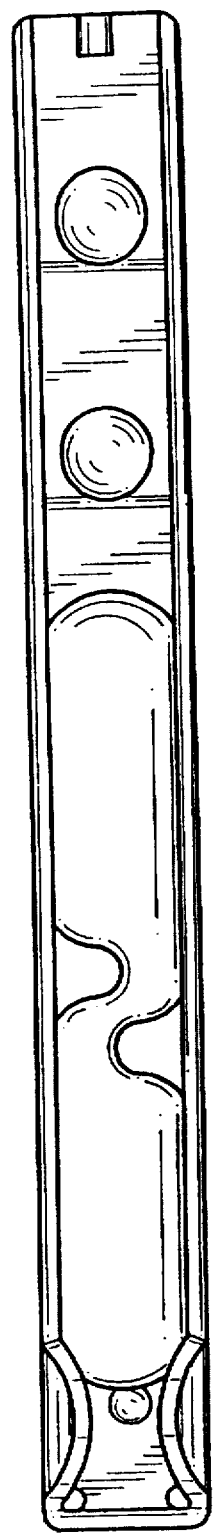
FIG. 25 is a bottom view of the reagent pack of FIG. 19.

In a preferred embodiment of the present invention, the tray 80 is inclined to its twenty degree limits only when the door 34 of the reagent handling system 30 is in the elevated or closed position. Otherwise, the tray 80 is inclined five degrees from horizontal such that the reagent pack forward end 100 is below the reagent pack rearward end 102. As illustrated in the simplified views of FIGS. 17 and 18, with the door 34 in the closed position, the angle of inclination of the front of the tray 80, the end of the tray which receives the slide 50 and reagent pack 62, varies from +20 degrees (FIG. 17) to −20 degrees (FIG. 18), relative to horizontal. Other angular offsets are possible in alternative embodiments. The sensors 179 provide an indication of when the tray 80 is at the limits of inclination.

When the door 34 is lowered, exposing the reagent packs 62 in the enclosure 40, the inclination motor 170 angles the front of the tray to +5 degrees above horizontal, referred to as an aspirate position, to facilitate removal and installation of reagent packs 62. This angle is illustrated in FIG. 16. Specifically, by locating depressions 128 in the pack floor surface 118 proximate the rear of each chamber, and by canting the floor 118 toward each such depression 128, complete aspiration of reagent contained within each chamber is achieved.

As shown in FIG. 2, a slide 50, disposed on the tray 80 in the aspirate position, is pulled out of the enclosure 40 to provide access to the reagent pack 62 stored thereon. As previously noted, the resilient arm 70 of the slide 50 is retained within tray lower half slot recesses 88a, 88b, maintaining the slide in either of the positions illustrated in FIG. 2.

In one embodiment of the present invention, the tray 80 and associated reagent packs 62 are cycled between the extreme inclination limits five times for approximately six seconds, then are maintained at the aspirate position for nine seconds. Such agitation, combined with the provision of mixing baffles 122 in at least one of the reagent pack chambers 120, allows the present system reagent handling system 30 to accept a reagent pack having a settled solid phase reagent in one chamber 120 and to provide such the solid phase reagent in fully suspended form by the time an assay requires the reagent.

It is while in the aspirate position of FIG. 16 that the plural reagent probes 150 access the underlying reagents through the lid apertures 142, 144, 146. As previously noted, when a reagent pack 62 is being accessed by a probe 150, an associated optical annunciator 66 is illuminated to indicate that the pack 62 should not be removed.

These and other examples of the invention illustrated above are intended by way of example and the actual scope of the invention is to be determined from the following claims.

What is claimed is:

1. A reagent handling system comprising plural reagent packs, each reagent pack comprising:
   plural chambers formed by opposing and parallel end walls, opposing and parallel side walls substantially orthogonal to said end walls, a floor surface attached to said end and side walls proximate a lower edge thereof, and at least one intermediate wall substantially parallel to said end walls and disposed between said side walls, wherein said end, side and intermediate walls define a pack upper edge; and
   mixing baffles disposed within at least one of said chambers operative to cause mixing of said fluids within said at least one chamber as fluid i s passed by said baffles, a first one of said baffles disposed opposing and proximate a second one of said baffles such that a throat region having a pair of converging then diverging walls is defined between said first one and said second one of said baffles.

2. The reagent handling system according to claim 1, wherein each of said mixing baffles is disposed on a respective one of said side walls from said floor surface to said pack upper edge.

3. The reagent handling system according to claim 1, wherein one of said mixing baffles is disposed more proximate said first end than another of said mixing baffles.

4. The reagent handling system according to claim 1, wherein said mixing baffles divide one of said plural chambers into two sub-chambers having substantially equal volume, said sub-chambers interconnected by the throat region formed between said baffles.

5. The reagent handling system according to claim 1, wherein each of said mixing baffles extends over halfway across said reagent pack between said side walls.

6. The reagent handling system according to claim 1, wherein said floor surface has a plurality of depressed regions, each of said depressed regions associated with a respective one of said plural chambers.

7. The reagent handling system according to claim 6, wherein said reagent pack further comprises a lid having plural penetrable regions, said lid disposable on said pack upper edge for completely covering said plural chambers.

8. The reagent handling system according to claim 7, wherein said plural penetrable regions are each aligned above a respective one of said plural chambers.

9. The reagent handling system according to claim 7, wherein said plural penetrable regions are each formed from at least one penetrable film.

10. The reagent handling system according to claim 1, further comprising a plurality of reagent pack slides, each of said slides for slidably transporting a respective reagent pack disposed thereon within said reagent handling system.

11. The reagent handling system according to claim 10, further comprising a tray for slidably retaining said plurality of reagent pack slides in a side by side configuration along a first axis.

12. The reagent handling system according to claim 11, further comprising an inclination drive and hinge mechanically connected to said tray for selectably inclining said tray about said first axis passing through said hinge.

13. The reagent handling system according to claim 12, further comprising at least one reagent probe carrier having at least one reagent probe, said at least one probe carrier translatable along said first axis proximate said tray for selectably disposing said at least one reagent probe into a selected one of said reagent packs.

14. The reagent handling system according to claim 13, said inclination drive further comprising an aspirate position defined by said tray inclined with respect to horizontal, wherein a low point of said floor surface is substantially vertically aligned with said at least one reagent probe.

15. The reagent handling system according to claim 13, said least one reagent probe carrier further comprising drive means for translating said at least one reagent probe along an axis orthogonal to said first axis and substantially parallel to said reagent pack side walls for selectably disposing said at least one reagent probe into a selected one of said chambers.

16. The reagent handling system according to claim 12, further comprising a cooling means in communication with said tray through said hinge to implement a tray cold plate for cooling reagent packs disposed thereon.

17. A reagent handling system comprising plural reagent packs, each reagent pack comprising:
   first and second ends defined by substantially vertical first and second end walls, respectively, and substantially vertical first and second side walls disposed there between, said end walls and said side walls having an upper edge and a lower edge;
   a floor surface sealably attached to said first and second end walls and said first and second side walls, said floor surface disposed proximate said lower edge;
   at least one intermediate wall disposed transverse said reagent pack from said first side wall to said second side wall, said intermediate wall intermediate said end walls and extending from said floor surface to said upper edge; and first and second mixing baffles each disposed on a respective one of said side walls and extending toward another of said side walls, both of said baffles disposed on a like side of said at least one intermediate wall, wherein one of said baffles is more proximate said first end then another of said baffles and wherein said baffles are disposed proximate one another such that a throat region having a pair of converging then diverging walls is defined between said baffles.

18. The reagent handling system according to claim 17, wherein said end walls, said side walls, said at least one intermediate wall, and said floor surface define a plurality of chambers open at said upper edge.

19. The reagent handling system according to claim 18, wherein said floor surface has a plurality of depressed regions, each of said depressed regions associated with a respective one of said chambers.

20. The reagent handling system according to claim 19, wherein said floor surface within each of said chambers slopes toward said respective depressed region.

21. The reagent handling system according to claim 17, wherein each of said baffles extends from said floor surface to said side wall upper edge.

22. The reagent handling system according to claim 21, wherein said baffles divide one of said plurality of chambers into two sub-chambers having substantially equal volume, said sub-chambers interconnected by the throat region formed between said baffles.

23. The reagent handling system according to claim 17, wherein each of said baffles extends over half the distance between said side walls.

24. The reagent handling system according to claim 20, wherein said reagent pack further comprises a lid having plural penetrable regions, said lid disposable on said upper edge for completely covering said plurality of chambers.

25. The reagent handling system according to claim 24, wherein said plural penetrable regions are each vertically aligned above a respective chamber.

26. The reagent handling system according to claim 24, wherein said plural penetrable regions are each substantially aligned above a respective depressed region.

27. The reagent handling system according to claim 24, wherein said plural penetrable regions are each formed from at least one penetrable film.

28. The reagent handling system according to claim 17, further comprising a plurality of reagent pack slides, each of said slides for transporting a respective reagent pack disposed thereon within said reagent handling system.

29. The reagent handling system according to claim 28, further comprising a tray for slidably retaining said plurality of reagent pack slides in a side by side configuration along a first axis.

30. The reagent handling system according to claim 29, further comprising an inclination drive and hinge mechanically connected to said tray for selectably inclining said tray about said first axis and said hinge.

31. The reagent handling system according to claim 30, further comprising at least one reagent probe carrier having at least one reagent probe, said at least one probe carrier translatable along said first axis proximate said tray for selectably disposing said at least one reagent probe into a selected one of said reagent packs.

32. The reagent handling system according to claim 31, said inclination drive further comprising an aspirate position defined by said tray inclined with respect to horizontal, wherein a low point of said floor surface is substantially vertically aligned with said at least one reagent probe.

33. The reagent handling system according to claim 31, wherein said at least one reagent probe carrier further comprises drive means for translating said at least one reagent probe along an axis orthogonal to said first axis and substantially parallel to said reagent pack side walls.

34. The reagent handling system according to claim 30, further comprising a cooling means in communication with said tray through said hinge to implement a tray cold plate for cooling reagent packs disposed thereon.

35. A reagent pack for providing fluent material, comprising:

an elongate enclosure having sides, ends and a bottom, said sides and ends having an upper edge and defining a chamber wit said bottom, said chamber for retaining said fluent material; and a plurality of baffles disposed within said chamber, said baffles operative to cause turbulence in said fluent material when said pack is rocked about a horizontal axis orthogonal to said sides, a first one of said baffles disposed opposing and proximate a second one of said baffles such that a throat region having a pair of converging then diverging side walls is defined between said first and second baffles.

36. The reagent pack according to claim 35, further comprising at least one intermediate wall disposed across said sides and defining, with said sides, ends and bottom, plural sub-chambers for retaining said fluent material.

37. The reagent pack according to claim 35, wherein said bottom further comprises a depression disposed within said chamber.

38. The reagent pack according to claim 35, wherein said baffles divide said chamber into portions connected by the throat region defined by said baffles.

39. The reagent pack according to claim 38, wherein one of said baffles is more proximate a first end than another of said baffles.

40. The reagent pack according to claim 35, further comprising a lid disposable on said upper edge.

41. The reagent pack according to claim 40, said lid further comprising a plurality of apertures, each of said apertures simultaneously disposable over a respective one of said chambers.

* * * * *